United States Patent [19]

Shieh

[11] Patent Number: 5,522,977
[45] Date of Patent: Jun. 4, 1996

[54] GLUCOSE SENSOR

[75] Inventor: Paul Shieh, Fremont, Calif.

[73] Assignee: Biomedix, Inc., Fremont, Calif.

[21] Appl. No.: 319,618

[22] Filed: Oct. 7, 1994

[51] Int. Cl.$^6$ .................. G01N 27/327; G01N 27/333
[52] U.S. Cl. .................. 204/403; 204/418; 205/778
[58] Field of Search .................. 204/403, 416, 204/418, 419, 153.12

[56] References Cited

U.S. PATENT DOCUMENTS

| | | | |
|---|---|---|---|
| 4,545,382 | 10/1985 | Higgins | 128/635 |
| 4,810,331 | 3/1989 | Garrison et al. | 204/418 |
| 4,830,959 | 5/1989 | McNeil | 435/7 |
| 4,882,013 | 11/1989 | Turner | 204/153.12 |
| 5,173,165 | 12/1992 | Schmid | 204/403 |
| 5,312,590 | 5/1994 | Gunasingham | 422/82.03 |
| 5,378,332 | 1/1995 | Pandey | 204/403 |

OTHER PUBLICATIONS

Kulys et al, *Biochim. Biophys. Acta*, 1983, 744, pp. 57–63 month unavailable.
Albery et al, *J. Electroanal. Chem.*, 1985, 194, pp. 223–235 month unavailable.
McKenna et al, *Anal. Chem.*, 1987, 59, pp. 954–958 month unavailable.
Hale et al, *Mol. Cryst. Liq. Cryst.*, 1988, 160, pp. 269–279 month unavailable.
Hale et al, *Synth. Met.*, 1989, 28, pp. 853–858 month unavailable.
Hale et al, "J. of the Am. Chem. Soc.", vol. 111, No. 9, (1989), pp. 3482–3484 month unavailable.
Kulys, "Biosensors", vol. 2, No. 1, (1986), pp. 3–13 month unavailable.
Kulys, et al, "Glucose Oxidase Electrode Based On Graphite and Methlthio Tetrahiatfulvalene As Mediator".
Analytical Letters, 26(12), 1993, pp. 2535–2542 month unavailable.
Nguyen, et al, "Development of Mediated Amperometric Biosensors for Hypoxanthine, Glucose and Lactate: A New Format".
Biosensors & Bioelectronics, vol. 8, 1993, pp. 421–431 month unavailable.

*Primary Examiner*—T. Tung
*Attorney, Agent, or Firm*—Marvin S. Aronoff

[57] ABSTRACT

A redox electrode for the rapid detection of glucose in aqueous media and a method for its use are provided. The redox electrode comprises an electrically conductive member such as copper, and a redox membrane in direct contact with said electrically conductive member. The redox membrane comprises a polymer matrix such as PVC containing a plasticizer, and a complex of 7,7,8,8-tetracyanoquinodimethane and tetrathiafulvalene with the complex having a burgundy-red coloration and characterized by a broad absorption from about 340 nm to about 550 nm and weaker absorption between about 650 nm to about 800 nm having about six small peaks with an absorption maximum at about 750nm. Glucose is rapidly assayed by bringing the redox electrode and a reference electrode into simultaneous contact with an aqueous medium containing KCl, phosphate buffer, glucose oxidase, peroxidase, and 3,3',5,5'-tetramethylbenzidine dihydrochloride. The potential of the redox membrane is then monitored until it is stable. A sample containing glucose is added to the aqueous medium, and the change of potential of the redox electrode, which is related to glucose concentration, is then observed. In a variant of this method, the redox electrode is treated with ascorbic acid before a glucose oxidation to magnify the potential difference generated, and after oxidation to rapidly collapse the potential and prepare the electrode for another analysis.

14 Claims, 3 Drawing Sheets

GLUCOSE SENSOR

BACKGROUND OF THE INVENTION

Although there are numerous methods for the quantitative determination of glucose in biological fluids, there is a need for a simple, rapid, highly sensitive, accurate and reproducible means which can be easily miniaturized, inexpensively produced, and which is inexpensive to use. Such means would be especially useful, convenient and less painful to the patient when screening for and monitoring diabetes in the human if only a few drops of blood were required for a reliable test. The usefulness of such means would be enhanced if it had sufficient sensitivity and accuracy to be applied to the quantitative determination of glucose concentrations in urine, which generally are far lower than in the blood. In addition, a simple, rapid, economical and convenient means which can be applied to the on-site monitoring of glucose concentrations during food processing and in agricultural products is needed.

For the foregoing reasons there is a need for a device for quantitative assay of glucose in biological and other fluids which is simple to use, delivers the assay rapidly, is highly sensitive, accurate and reproducible, and which can be easily miniaturized, inexpensively produced and inexpensively used.

BRIEF DESCRIPTION OF THE INVENTION

The present invention is directed to providing a redox electrode with high sensitivity and rapid response which in conjunction with an external enzyme system provides an improved means for detection of glucose in biological fluids such as human blood or urine.

Yet another object of the present invention is to provide a redox electrode for detection of glucose in biological fluids which may be readily miniaturized, is easy and economical to manufacture and may be incorporated in diagnostic kits or used as a sensor in an automated system.

The above and other objects are achieved in accordance with the present invention by providing a coated wire redox electrode which when immersed together with a calomel or silver-silver chloride reference electrode in an aqueous solution comprising an enzyme such as glucose oxidase, an enzyme such as hydrogen peroxidase, a dye such as TMB, and an electrolyte salt such as KCl or a phosphate buffer, can be used to assay, by means of the electrical potential generated, the quantity of glucose in an aqueous fluid admixed with said aqueous solution.

An embodiment of the redox electrode of the present invention comprises a coated wire electrode having a sensing membrane made of plasticized PVC and containing a TTF/TCNQ complex made by mixing equal parts by weight of TTF and TCNQ in a solvent and concentrating the solution in the presence of an undissolved particle of TCNQ to form a burgundy-red solution. The redox electrode is produced by using this solution to form a membrane at the tip of an insulated wire. Polymeric materials and plasticizers preferred for the formation of the redox membrane, as well as a description of the process of forming an electrode with an insulated conductor and the membrane formulation are given in U.S. patent application Ser. No. 08/103193, now U.S. Pat. No. 5,401,377 which is incorporated herein by reference.

DESCRIPTION OF THE PREFERRED EMBODIMENTS

Figure 1:
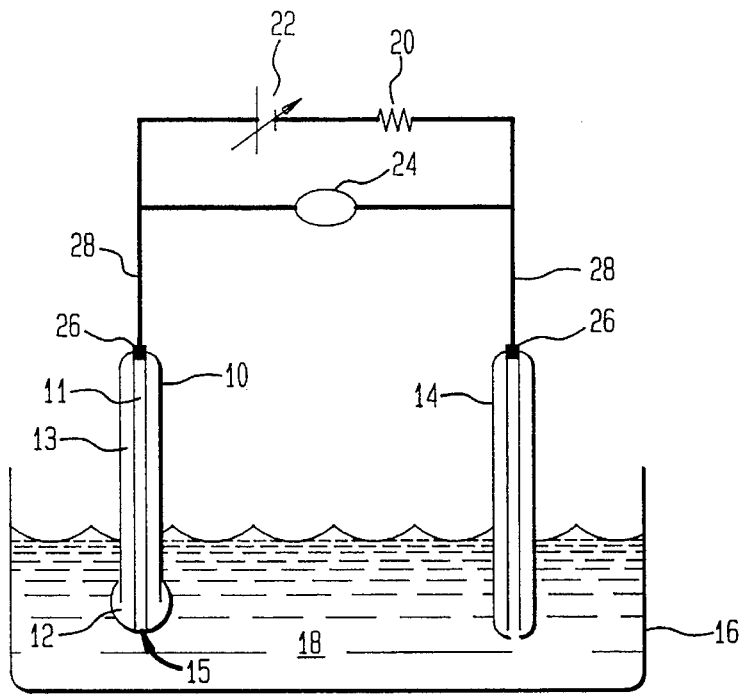
FIG. 1 is a cross-sectional view of an electrolytic cell used for the detection of glucose.

The following abbreviations used in the description of different embodiments of the invention are hereby defined:
TCNQ—7,7,8,8-Tetracyanoquinodimethane
TTF—Tetrathiafulvalene
TMB—3,3', 5,5'-Tetramethylbenzidine dihydrochloride
THF—Tetrahydrofuran
PVC—Polyvinylchloride FIG. 1 is a cross-sectional view of a typical electrolytic cell used for the detection of glucose in one embodiment of the present invention.

The cell comprises an aqueous chamber 16 which contains an aqueous solution or dispersion 18 of the reagents to be used in the assay and the substance to be assayed.

Immersed in the aqueous solution 18 are a sensing electrode 10 and a reference electrode 14.

The sensing electrode 10 and the reference electrode 14 are electrically connected at their non-immersed ends via separate lengths of electrical conductor 28, through an electrical circuit having an electrometer 24. The reference electrode 14 is typically either a standard calomel electrode or a silver-silver chloride reference electrode. A variable resistor 20, and a potentiometer 22 are optionally connected across the cell prior to a glucose assay in order to determine membrane resistance Rm as described below.

The sensing electrode 10 is generally a coated wire electrode and includes an electrically conductive member which in this embodiment is a core member 11, an electrical insulation layer 13, and a redox membrane 15, formulated in the manner described below.

In practice, the core member 11 is comprised of wire made of copper, which is preferred, but silver, conductive carbon, gold, aluminum, platinum, nickel, stainless steel, iron and other conductive materials and mixtures or coatings thereof can be used. Copper wire of 12–26 gauge is preferred with 18–24 gauge more preferred to obtain a miniature electrode on a convenient base. The body of the conductive core member 11, except the exposed tip 15, is sheathed by the electrical insulation layer 13. In practice, the electrical insulation layer 13 is comprised of PVC, but copolymers of PVC, polymers generally belonging to the PVC family and other polymers compatible with PVC and mixtures thereof and, polyethylene, polypropylene, nylon, polytetrafluoroethylene, copolymers of tetrafluoroethylene with ethylene and propylene, silicone rubber, and other electrical insulating materials may be used. However, insulating materials comprised of PVC, copolymers of PVC and polymers compatible with PVC are preferred.

The uninsulated zone of the conductive core 11, the exposed tip 15, is completely coated with the redox membrane 16, prepared in the manner described below, which adheres to it in some degree and, is generally more strongly adherent to the electrical insulation layer 13 which it overlays. The membrane 15 may overlay insulation layer 13 to any extent necessary to provide sufficient mechanical strength and overall adhesion to insulation layer 13, but an overlay generally adjacent to tip 18 is preferred as this uses less material and facilitates handling.

In general the base material for the membrane 12 is a polymer matrix. The polymer is preferably PVC, copolymers of PVC or other non-polar, relatively water insoluble polymers such as polyvinyl butyryl, polyvinylidene chloride, polyvinyl fluoride, polyvinylidene fluoride, polyvinyl bromide, polyvinylidene bromide, copolymers of polyvinyl alcohol with an appropriate comonomer such that the copolymer is insoluble, polymethyl methacrylate and copolymers thereof, epoxy resins, polyurethanes, poly(fluorophosphazenes), block copolymers of poly(dimethylsiloxane) and polystyrene, polyamides, polyimides and silicone rubber. For electrode embodiment 10 of FIG. 1, a polymer which is generally of sufficiently similar composition to that comprising the electrical insulation layer 13, so that it is adherable to the insulation, is more preferred. PVC and polymers based on PVC are most preferred for the polymer matrix of the redox membrane 12 when the electrical insulation layer 13 comprises PVC or polymers based on PVC.

Figure 4A:
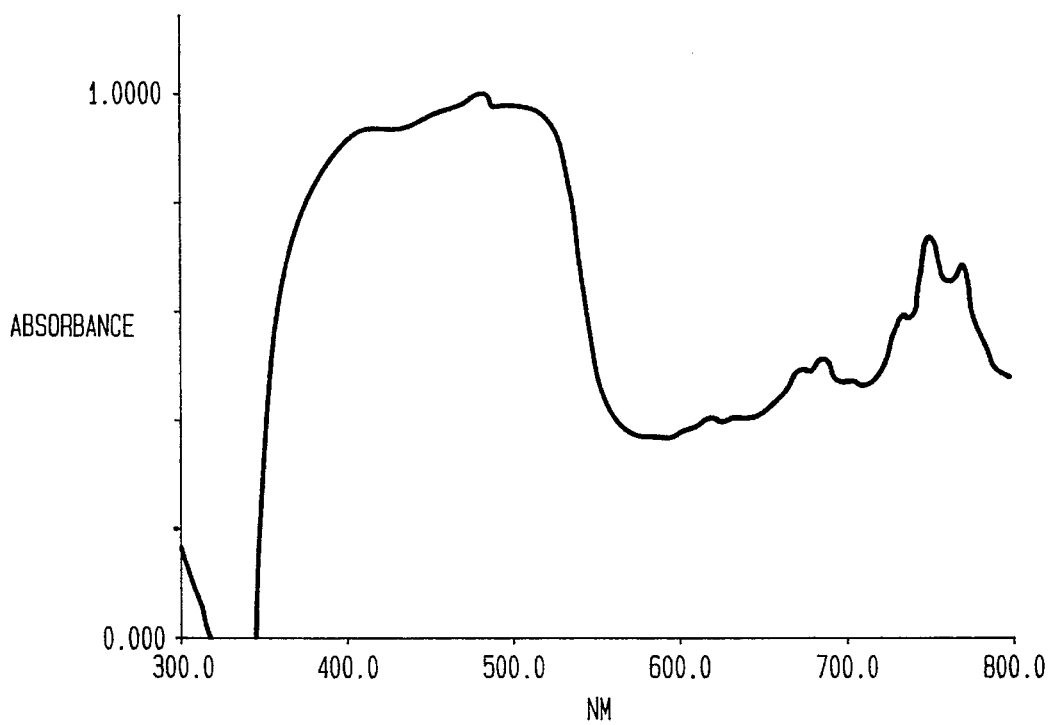
FIG. 4A is an absorption spectrum of burgundy-red TCNQ/TTF complex.
Figure 4B:
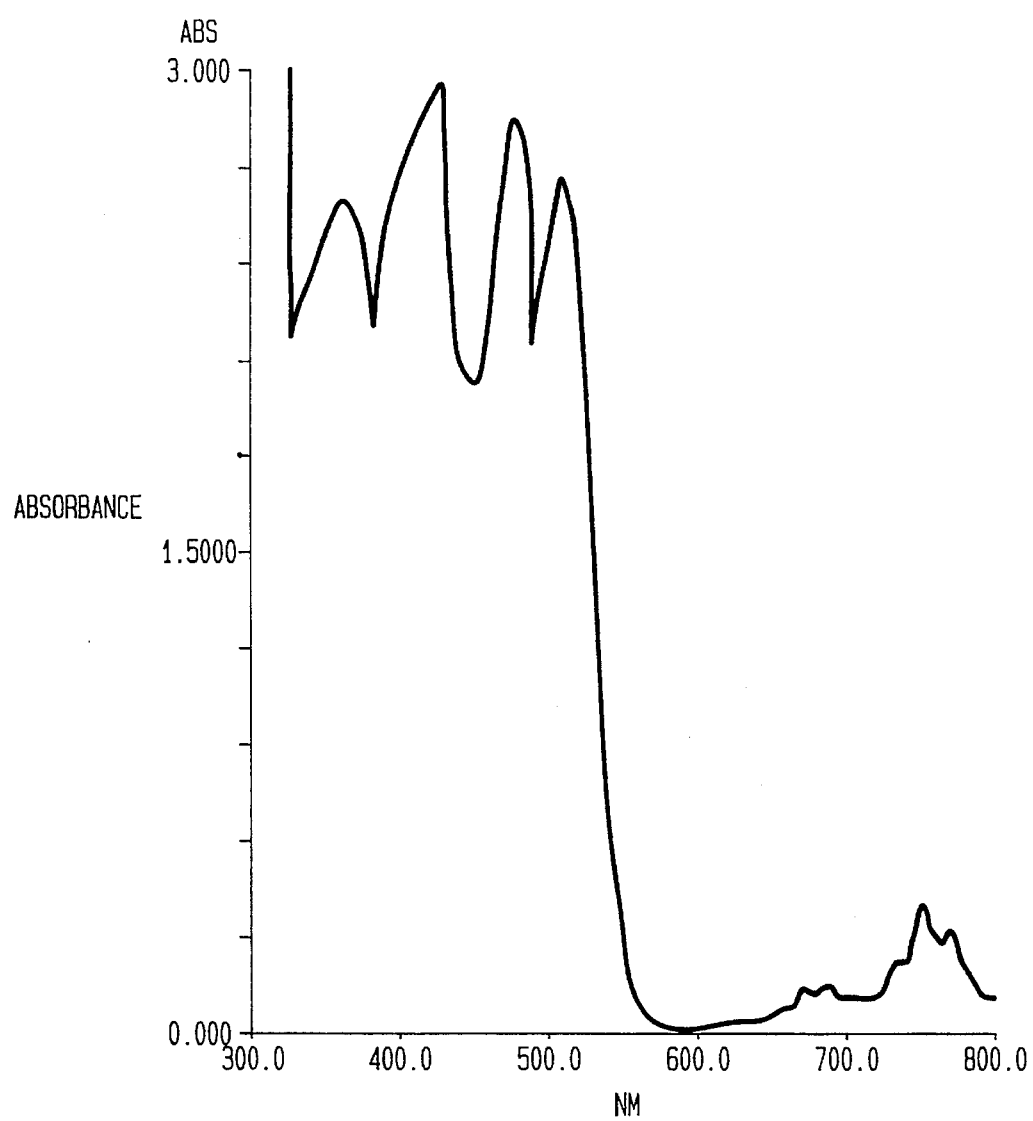
FIG. 4B is an absorption spectrum of green TCNQ/TTF complex.

A complex of TCNQ and TTF must be present in the polymeric membrane of the electrode. The TCNQ-TTF complex having a green color makes a far less effective glucose sensor than the TCNQ-TTF complex having a burgundy-red coloration which is most preferred as it produces a delta Vm which increases in proportion to increasing glucose concentration, the fastest response and the most reproducible results. The TCNQ-TTF complex having a green color is characterized by an absorption spectrum having at least four absorption maxima between about 325 nm to about 550 nm and much weaker absorption between about 600 nm to about 800 nm relative to the absorption maxima between about 325 nm to about 550 nm. This is shown in FIG. 4B.

The TCNQ-TTF complex having a burgundy-red coloration is characterized by a broad absorption from about 340 nm to about 550 nm and weaker absorption between about 650 nm to about 800 nm having about six small peaks with an absorption maximum at about 750 nm. This is shown in FIG. 4A.

In order to assay for glucose, the redox electrode and reference electrode were immersed in an aqueous solution containing a volume ratio of about 0.2 parts 0.1M KCl to about 0.8 parts 0.1M phosphate buffer mixture, glucose oxidase (*Aspergillus niger*, Sigma G-6766), peroxidase (Toyobo Co., 126 units/mg) and TMB dye. KCl concentrations are generally about 0.01M to about 1.0M with concentrations of about 0.025M to about 0.1M preferred. Glucose oxidase concentrations are generally about 0.125 to about 12.5 units per ml with concentrations of about 0.2 to about 1 unit per ml preferred. Hydrogen peroxidase concentrations are generally about 0.01 to about 12.5 units per ml with concentrations of about 0.1 to about 1 unit per ml preferred. A phosphate buffer having a concentration of about 100 mM and a pH of about 6.8 is preferred in making standard solutions of the enzymes. TMB concentrations are generally about 0.05 mg/ml to about 20 mg/ml with concentrations of about 0.1 mg/ml to about 5 mg/ml preferred. Concentrations of the reagents within the preferred ranges generally give fast glucose oxidation. A sample containing glucose is then mixed into this solution.

The key elements controlling the speed of glucose readout in the present procedure are: enzyme activity, the amount of dye present and the presence in the polymeric membrane film of a TCNQ/TTF complex having a burgundy-red coloration. The scheme of the glucose oxidation reaction mechanism can be represented as follows:

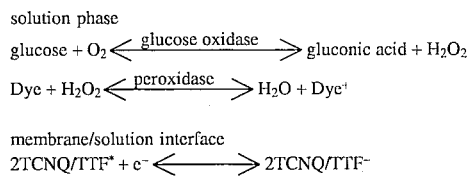

In this scheme TCNQ/TTF* can be involved in the redox reaction via electron transfer or can function as a conductive species in the sensor to detect formation of positively charged TMB dye at the membrane/solution interface.

A process for making an embodiment corresponding to electrode 10 of FIG. 1, generally comprises the steps of, preparing a fresh conductive surface by cutting through the insulation 13 and the conductive core 11 of an insulated metallic wire thereby exposing a fresh metallic surface at the tip 18; preparing a liquid solution of a redox membrane formulation containing a polymer, solvent, plasticizer, and a redox couple; completely coating the exposed metallic tip 15 and the insulation layer 13 adjacent to it, by immersing the tip 15 and the adjacent insulation layer in the liquid solution of a redox membrane formulation; and, evaporating the solvent from the coating to form a redox membrane 16 at the tip 15, of electrode 10. Generally, one coating of redox membrane formulation will give the redox membrane 12 sufficient thickness for mechanical stability. However, the coating step may be repeated as many times as necessary to provide the redox membrane 12 with sufficient thickness for mechanical stability.

In the cutting step any device such as conventional hand held wire cutters, a chromatography cutter or any machine which can cut wire or which is capable of cutting through the insulating layer 13 and the conductive core 11 thereby exposing a fresh surface of the conductive core 11 and creating the exposed conductor tip 15 may be used. The cut surface may in general be of any geometry but a generally flat planar surface for exposed conductor tip 15 is preferred. In the case of a coated wire electrode a configuration in which the exposed conductor tip 15 created by cutting through insulating layer 13 and conductive core 11 has a generally flat planar surface which is generally perpendicular to the longitudinal axis of conductive core member 11 is most preferred, as this provides a base on which the membrane 12 can be formed with relatively uniform thickness.

The following example will show how the redox membrane formulation is made and how it is used to make an embodiment of the invention:

EXAMPLE 1

This example shows how to construct a sensor for glucose. A membrane forming solution was prepared by mixing the following components:

600 mg of a 5% PVC solution in THF
70 mg dibutylphthalate plasticizer
50 mg of 1% TCNQ in THF
50 mg of 1% TTF in THF.

The membrane forming solution was reduced to about half its original volume by allowing the solvent to evaporate in air at ambient temperature for about 3 hours. During this time TCNQ and TTF formed a dark burgundy-red complex, and the solution became very viscous. Formation of the burgundy-red colored TCNQ-TTF complex is accelerated by adding an undissolved TCNQ particle to the membrane forming solution before evaporation. The burgundy-red TCNQ-TTF complex is characterized by the ultraviolet spectrum shown in FIG. 4A.

To form the burgundy-red complex, a minute quantity of undissolved TCNQ, generally a particle, is taken from the bottom of the, 1% TCNQ solution and added to the membrane forming solution containing TCNQ-TTF within a short time after the formation of the membrane forming solution. Generally, the TCNQ particle is added to the membrane forming solution immediately after TCNQ and TTF solutions have been added. The 1% TCNQ solution is made by dissolving TCNQ in THF at room temperature.

Formation of a burgundy-red TCNQ-TTF complex is a key factor in obtaining the most effective sensor. TCNQ obtained from Aldrich Chemical gave the best results. A greenish TCNQ-TTF complex, which makes a far less effective glucose sensor, was generally formed in the absence of an undissolved TCNQ particle when TCNQ solution concentration was too high, or in the presence of too much undissolved TCNQ. Use of a TCNQ solution having a concentration above about 2% in the membrane forming solution formulation of Example 1 produced the green colored complex. The green colored complex was also produced when the membrane forming solution formulation of Example 1 was used and several undissolved TCNQ particles having total weight above about 10 mg were added. In the absence of an added particle of TCNQ, the membrane forming solution of Example 1 forms an orange-brown colored complex. Excess plasticizer can also produce the orange-brown colored complex.

A PVC insulated 24 gauge copper wire (Woods® No. 347, Woods Wire Products Inc.) was freshly cut with a pair of sharp wire cutters to attain a flat, clean copper surface at the tip surrounded by PVC. The wire was then coated with the above membrane forming composition by dip coating twice. The wire was held in a vertical position while dip coating and the membrane forming solution coated the exposed metal and about 2–3 mm of the adjacent PVC insulation. The membranes were then air dried overnight to remove solvent.

The membrane formulation of Example 1 may also be used to coat uninsulated wire to form more conventional wire electrodes as described in detail by R. W. Cattrall and I. C. Hamilton in the article "Coated-Wire Ion-Selective Electrodes", Ion-Selective Electrode Rev., 1984, Vol. 6, pp. 125–172, incorporated herein by reference to the extent that it is pertinent. U.S. Pat. No. 4,948,473 also describes preparation of coated-wire electrodes and is incorporated herein by reference to the extent that it is pertinent. The membrane formulation of Example 1 may also be used to form a redox membrane on electrodes in which the resultant membrane is in electrical contact with an internal reference electrode element. The membrane formulation may also be separately coated on other substrates such as glass, metal, polytetrafluoroethylene and the like, and other surfaces from which the redox membrane may be released after evaporation of solvent.

Example 2 demonstrates a version of a procedure for quantitative determination of glucose and is illustrative of the procedure for urine, whole blood and blood serum:

EXAMPLE 2

This example illustrates the quantitative assay of glucose using the redox electrode of Example 1 in an electrolytic cell having the general configuration of FIG. 1.

The potential across the sensor electrode and reference electrode can be measured by standard means such as a volt meter or a high impedance electrometer.

Membrane resistance Rm is calculated by measuring the current through an external variable resistance Ri connected with a power supply having output Ei. Typically, a voltage 200 mV is applied and Ri is adjusted until the electrometer potential readout is half the value of Ei.

Rm is calculated by the following equation:

$$Rm = \frac{Vm\,Ri}{Ei - Vm}.$$

At Vm (membrane voltage)=½ Ei, Rm=Ri.

A membrane resistance of $10^6$ ohm or less is preferred to obtain the greatest membrane potential change in response to glucose oxidation.

The redox electrode and reference electrode were immersed in an aqueous solution composed of a 0.8 cc:0.2 cc volume ratio of 0.1M KCl and 0.1M phosphate buffer containing enzyme. The enzyme solution contained 5 units/ml glucose oxidase (*Aspergillus niger*, Sigma G-6766), 5 units/ml peroxidase (Toyobo Co., 126 units/mg) and 0.5 mg/ml TMB dye. Standard glucose solution (Sigma catalog no. 16-11) was added after a stable membrane potential was reached. The procedure was repeated for each glucose concentration indicated in FIG. 2.

Figure 2:
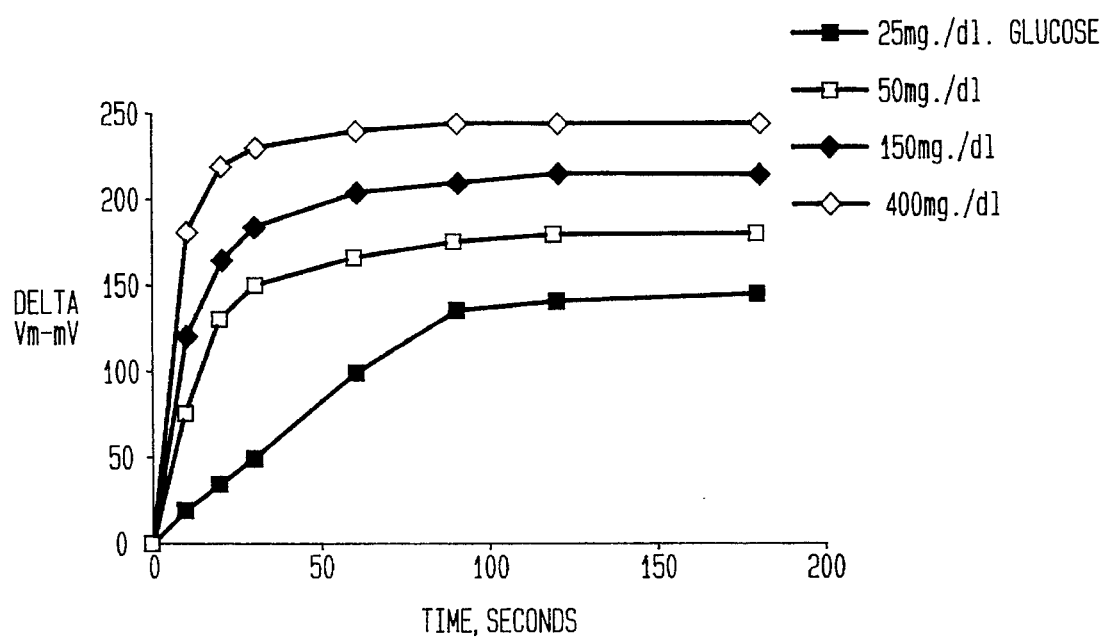
FIG. 2 is a graph of the time dependent response of a glucose sensor to various glucose concentrations.

The glucose concentration was measured by plotting the change of membrane potential, Delta Vm with time. FIG. 2 shows time dependent glucose responses at given glucose concentrations. At low glucose concentrations such as 25 mg/dl, 60 to 90 seconds are required to reach the maximum response. However at glucose concentrations of 50 mg/dl and higher, only 10–20 seconds are needed for the maximum response.

Figure 3:
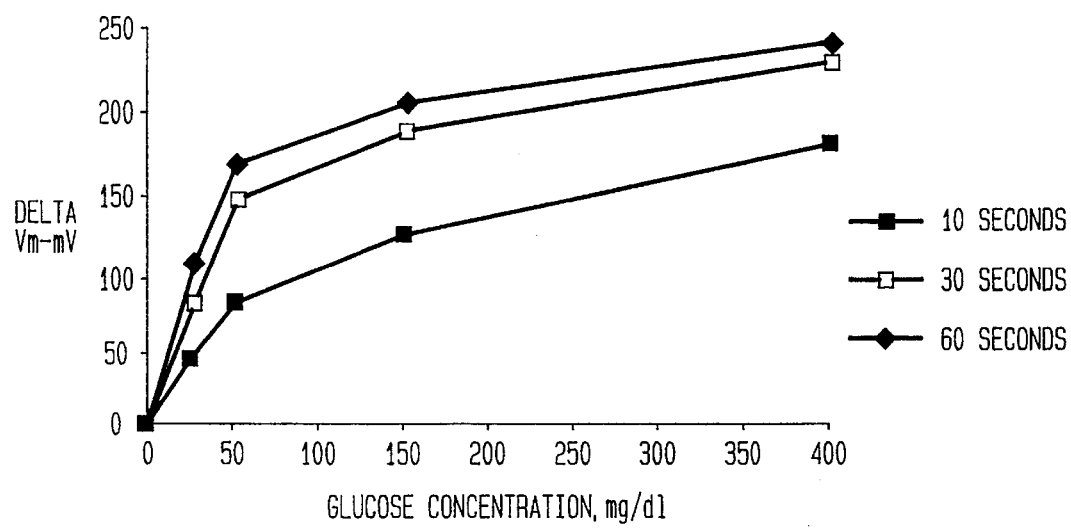
FIG. 3 is a graph of the response of a glucose sensor to various glucose concentrations at fixed times.

FIG. 3 shows plots of glucose response potential change, Delta vm, versus glucose concentration at readout intervals corresponding to 10, 30, and 60 seconds. The sensitivity is 1.3 mV/10 mg/dl glucose at 10 second readout and 12 mV/10 mg/dl glucose for 30 second readout. The selection of either 10, 30 or 60 second readout depends on the glucose concentration. For concentrations of 50 mg/dl and higher, reliable assays may be obtained in 30 to 60 seconds while concentrations of 25 mg or less may require 60 seconds or more for maximum precision.

Either detection method will provide an extremely rapid glucose assay.

In a further aspect of the present invention, the delta Vm is magnified by the addition of adjuvant substances to the test solution, or by washing the electrode with solutions of such substances which reduce the initial membrane potential of the glucose sensor.

The electrical field established by the glucose sensor during sensor preparation is responsible for the efficiency of glucose detection. This is so because the more positive the electric field is, the greater is the inhibition of potential increase produced by glucose oxidation. The less positive the electrical field, the greater the potential change induced by glucose oxidation.

The size of the electrical field in the sensor is determined by the concentration and ratio of TCNQ and TTF, the amount of plasticizer and the thickness of the membrane. In addition, the presence of compounds, such as ascorbic acid in the aqueous electrolyte solution also collapse this electrical field resulting in an enhancement of the potential change (delta Vm) induced by glucose oxidation. The effect of ascorbic acid is demonstrated in Example 3.

EXAMPLE 3

This example shows the effect of ascorbic acid in increasing the response of the glucose sensor prepared in Example 1 to glucose. The sensor was stored a few minutes in 0.1M ascorbic acid and then rinsed with deionized water. The potential change induced by glucose, under conditions similar to those of Example 2, were examined. Table 1 shows that the ascorbic acid treated sensor exhibits a greater positive potential, and thus a greater delta Vm over a range of glucose concentrations than the untreated glucose sensor.

TABLE 1

Comparison of Potential Changes With Glucose Concentration of Ascorbic Acid Treated Versus Untreated Glucose Sensor
$Rm = 10^6$ ohm

| GLUCOSE CONC. | CONTROL | | ASCORBIC ACID (0.1M) TREATMENT | |
| --- | --- | --- | --- | --- |
| (mg/dl) | Vm, mV | V, mV | Vm, mV | V, mV |
| 0 | 129 | 0 | 4 | 0 |
| 50 | | +46 | | +59 |
| 150 | | +145 | | +171 |
| 250 | | +171 | | +250 |

After the measurement, the sensor can be treated with ascorbic acid again to maintain the reversibility of potential generation by glucose. In this manner, the sensor can be used as many times as needed for glucose detection. Charge build up can also be dispersed by replacing the medium with deionized water and rinsing a few times. However, ascorbic acid treatment has the advantage of giving the lowest initial electrode potential.

The previously described versions of the present invention have many advantages, including ease and simplicity of preparation and use. They may be readily made in a few steps from inexpensive materials such as insulated copper wire by simply cutting it and dip coating the newly created metallic surface with a readily formulated membrane forming solution. The simplicity of this process which is done in relatively few steps makes for a high degree of consistency among individual sensors and from batch to batch. Another advantage is the higher degree of mechanical stability achieved as a consequence of good adhesion of the polymeric membrane to the surface of the underlying conductor and to the layer of insulation covering the conductor.

The procedure for assaying glucose utilizes an enzyme system separate from the electrode itself which is externally added. The sensor itself and the reagents for glucose assay thereby have long shelf life.

Yet another advantage is that the high sensitivity of the sensor makes it possible to reliably assay even low concentrations of glucose in very small volumes of test media such as biological fluids. Thus, for example, a drop of blood may be rapidly assayed in minutes in a physicians office without the need to take several milliliters of blood from the patient and send this sample out for analysis. The high sensitivity of the sensor also makes it possible to quantitatively monitor glucose levels by testing the patients urine, thus avoiding the need to draw blood.

Still another advantageous feature is that the active sensor surface of versions of the present invention may be confined to about the area of the cross-section of a fine wire thus facilitating miniaturization.

A further advantage of versions of the present invention is that since they can be made by a simple, inexpensive process from low cost materials or very small quantities of more expensive materials, from an economic point of view, they may be disposed of after even a single use if this is desired.

Although the present invention has been described in considerable detail with reference to certain preferred versions thereof, other versions are possible. For example, other versions of the sensor are possible as is its use in conjunction with instrumentation such as titrimetric devices for determination of glucose in media such as biological fluids, foodstuffs and waste streams. Therefore, the spirit and scope of the appended claims should not be limited to the description of the preferred versions contained herein.

What is claimed is:

1. An electrode for the potentiometric determination of glucose in aqueous media comprising:
    an electrically conductive member, and
    a redox membrane indirect contact with said electrically conductive member, said redox membrane comprising;
        a polymer matrix, said polymer matrix containing;
            a plasticizer, and
            a complex of 7,7,8,8-tetracyanoquinodimethane and tetrathiafulvalene comprising a complex having a burgundy-red color.

2. The electrode of claim 1 in which the complex of 7,7,8,8-tetracyanoquinodimethane and tetrathiafulvalene comprises a complex having an ultraviolet absorption spectrum with broad absorption from about 340 nanometers to about 550 nanometers.

3. The electrode of claim 1 in which said polymer matrix comprises polyvinylchloride and the plasticizer comprises dibutylphthalate.

4. The electrode of claim 3 in which said electrically conductive member comprises a wire having a tip, with said redox membrane in direct contact with said tip.

5. The electrode of claim 4 in which the wire comprises copper.

6. The electrode of claim 5 in which said wire further comprises a layer of insulation with said layer of insulation sheathing said copper wire along its length.

7. The electrode of claim 6 in which said polymer matrix adheres to said layer of insulation sheathing the copper wire.

8. A polymeric redox membrane for potentiometric determination of glucose, the membrane to interface with a test solution containing glucose, the membrane in direct contact with a conductive substrate or in electrical contact with an internal reference electrode element, said membrane comprising:
    a polymeric matrix, the polymeric matrix containing;
        a plasticizer, and
        a complex of 7,7,8,8-tetracyanoquinodimethane and tetrathiafulvalene comprising a complex having a burgundy-red color.

9. The polymeric redox membrane of claim 8 in which the complex of 7,7,8,8-tetracyanoquinodimethane and tetrathiafulvalene comprises a complex having an ultraviolet absorption spectrum with broad absorption from about 340 nanometers to about 550 nanometers.

10. The polymeric redox membrane of claim 8 in which the polymeric matrix comprises polyvinylchloride.

11. The polymeric redox membrane of claim 10 in which the plasticizer comprises dibutylphthalate.

12. A redox membrane for the potentiometric assay of glucose in aqueous solution, fabricated in steps comprising:
    a) preparing a liquid solution of polyvinylchoride, dibutylphthalate and equal weights of 7,7,8,8-tetracyanoquinodimethane and tetrathiafulvalene in a solvent;
    b) adding a particle of solid 7,7,8,8-tetracyanoquinodimethane to the solution of step a);
    c) concentrating the solution of step b) at ambient temperature until the solution has a burgundy-red coloration and a higher viscosity;

d) coating the solution of step c) on a substrate;
e) evaporating the solvent from the coating of step d) to form a redox membrane.

13. The redox membrane of claim 12 in which the solvent of step a) is tetrahydrofuran.

14. A complex useful as a component of redox membranes for potentiometric glucose sensors comprising:

a complex of 7,7,8,8-tetracyanoquinodimethane and tetrathiafulvalene formed in solution in the presence of undissolved 7,7,8,8-tetracyanoquinodimethane, the complex having a burgundy-red color in solution and an absorption spectrum in solution with broad absorption from about 340 nanometers to about 550 nanometers.

* * * * *